(12) United States Patent
Hoang et al.

(10) Patent No.: US 7,488,757 B2
(45) Date of Patent: Feb. 10, 2009

(54) INVISIBLE ANTIMICROBIAL GLOVE AND HAND ANTISEPTIC

(75) Inventors: Minh Quang Hoang, Sandy, UT (US); Donald Edward Hunt, Provo, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 375 days.

(21) Appl. No.: 10/550,184

(22) PCT Filed: Mar. 24, 2004

(86) PCT No.: PCT/US2004/009009

§ 371 (c)(1),
(2), (4) Date: Jul. 24, 2006

(87) PCT Pub. No.: WO2004/084973

PCT Pub. Date: Oct. 7, 2004

(65) Prior Publication Data

US 2006/0263323 A1 Nov. 23, 2006

Related U.S. Application Data

(60) Provisional application No. 60/457,054, filed on Mar. 24, 2003.

(51) Int. Cl.
| | |
|---|---|
| *A01N 25/00* | (2006.01) |
| *C11D 3/00* | (2006.01) |
| *A61K 31/045* | (2006.01) |
| *A61K 31/047* | (2006.01) |
| *A61K 31/05* | (2006.01) |
| *A61K 31/14* | (2006.01) |
| *A61K 31/155* | (2006.01) |
| *A61K 31/23* | (2006.01) |
| *A61K 31/235* | (2006.01) |

(52) U.S. Cl. ............... 514/635; 510/132; 514/483; 514/544; 514/545; 514/552; 514/636; 514/637; 514/642; 514/724; 514/738

(58) Field of Classification Search .......... 424/404, 424/405; 510/132; 514/483, 545, 552, 635, 514/636, 637, 642, 724, 738

See application file for complete search history.

(56) References Cited

U.S. PATENT DOCUMENTS

| | | |
|---|---|---|
| 4,009,714 A | 3/1977 | Hammer |
| 4,066,556 A | 1/1978 | Vaillancourt |
| 4,294,594 A | 10/1981 | Sloane, Jr. et al. |
| 4,309,992 A | 1/1982 | Dodak et al. |
| 4,311,587 A | 1/1982 | Nose et al. |
| 4,374,126 A | 2/1983 | Cardarelli et al. |
| 4,416,772 A | 11/1983 | Sato et al. |
| 4,560,382 A | 12/1985 | Isono |
| 4,568,366 A | 2/1986 | Frederick et al. |
| 4,678,606 A | 7/1987 | Akhter et al. |
| 4,695,382 A | 9/1987 | Cronin |
| 4,702,829 A | 10/1987 | Polaschegg et al. |
| 4,714,556 A | 12/1987 | Ambrus et al. |
| 4,738,668 A | 4/1988 | Bellotti et al. |
| 4,787,974 A | 11/1988 | Ambrus et al. |
| 4,861,485 A | 8/1989 | Fecondini |
| 4,895,566 A | 1/1990 | Lee |
| 5,053,339 A | 10/1991 | Patel |
| 5,093,235 A | 3/1992 | Williams et al. |
| 5,217,493 A | 6/1993 | Raad et al. |
| 5,252,222 A | 10/1993 | Matkovich et al. |
| 5,312,813 A | 5/1994 | Costerton et al. |
| 5,366,505 A | 11/1994 | Farber |
| 5,512,199 A | 4/1996 | Khan et al. |
| 5,530,102 A | 6/1996 | Gristina et al. |
| 5,554,147 A | 9/1996 | Batich et al. |
| 5,556,760 A | 9/1996 | Nakamura et al. |
| 5,638,812 A | 6/1997 | Turner |
| 5,645,824 A | 7/1997 | Lim et al. |
| 5,716,406 A | 2/1998 | Farber |
| 5,723,132 A | 3/1998 | Tseng et al. |
| 5,788,687 A | 8/1998 | Batich et al. |
| 5,798,115 A | 8/1998 | Santerre et al. |
| 5,817,063 A | 10/1998 | Turnbull |
| 5,855,896 A | 1/1999 | Lim et al. |
| 5,906,834 A | 5/1999 | Tseng |
| 5,935,094 A | 8/1999 | Zupkas |
| 6,017,334 A | 1/2000 | Rawls |
| 6,022,551 A * | 2/2000 | Jampani et al. ............. 424/405 |
| 6,022,748 A | 2/2000 | Charych et al. |
| 6,048,337 A | 4/2000 | Svedman |
| 6,080,423 A | 6/2000 | Charych et al. |
| 6,106,287 A | 8/2000 | Yates |
| 6,132,765 A | 10/2000 | DiCosmo et al. |
| 6,159,007 A | 12/2000 | Sorensen |
| 6,171,496 B1 | 1/2001 | Patil |
| 6,180,135 B1 | 1/2001 | Charych et al. |
| 6,180,584 B1 | 1/2001 | Sawan et al. |

(Continued)

*Primary Examiner*—John Pak
*Assistant Examiner*—Nathan W Schlientz
(74) *Attorney, Agent, or Firm*—The Webb Law Firm

(57) ABSTRACT

An alcohol based hand surgical scrub, which includes cationic anti-microbial agent preservatives, cationic polymer film-forming agents and a skin emollient, and provides a long term residual, anti-microbial "invisible glove" on the skin. The composition provides an immediate reduction in bacterial microbes. The polymer system creates an invisible film on the skin following solvent evaporation. This invisible film provides a lasting anti-microbial barrier on the skin which acts to prevent microbial growth.

2 Claims, 1 Drawing Sheet

U.S. PATENT DOCUMENTS

| | | | |
|---|---|---|---|
| 6,228,393 B1 | 5/2001 | DiCosmo et al. |
| 6,257,265 B1 | 7/2001 | Brunner et al. |
| 6,259,074 B1 | 7/2001 | Brunner et al. |
| 6,277,652 B1 | 8/2001 | Jo et al. |
| 6,282,444 B1 | 8/2001 | Kroll et al. |
| 6,306,422 B1 | 10/2001 | Batich et al. |
| 6,306,598 B1 | 10/2001 | Charych et al. |
| 6,350,251 B1 | 2/2002 | Prosl et al. |
| 6,391,001 B1 | 5/2002 | Graham et al. |
| 6,395,561 B1 | 5/2002 | Charych et al. |
| 6,399,853 B1 | 6/2002 | Roe et al. |
| 6,423,219 B1 | 7/2002 | Chandler |
| 6,428,491 B1 | 8/2002 | Weiss |
| 6,436,885 B2 | 8/2002 | Biedermann et al. |
| 6,451,748 B1 | 9/2002 | Taylor et al. |
| 6,468,649 B1 | 10/2002 | Zhong |
| 6,471,689 B1 | 10/2002 | Joseph et al. |
| 6,475,434 B1 | 11/2002 | Darouiche |
| 6,475,516 B2 | 11/2002 | DiCosmo et al. |
| 6,479,727 B1 | 11/2002 | Roe |
| 6,501,002 B1 | 12/2002 | Roe et al. |
| 6,540,915 B2 | 4/2003 | Patil |
| 6,562,295 B1 | 5/2003 | Neuberger |
| 6,579,539 B2 | 6/2003 | Lawson et al. |
| 6,660,484 B2 | 12/2003 | Charych et al. |
| 6,666,842 B1 | 12/2003 | Sakai |
| 6,699,391 B2 | 3/2004 | Baldridge et al. |
| 6,713,660 B1 | 3/2004 | Roe et al. |
| 6,719,907 B2 | 4/2004 | Collins et al. |
| 6,719,991 B2 | 4/2004 | Darouiche et al. |
| 6,723,350 B2 | 4/2004 | Burrell et al. |
| 6,723,689 B1 * | 4/2004 | Hoang et al. ............ 510/130 |
| 6,731,971 B2 | 5/2004 | Evans, III et al. |
| 6,758,971 B1 | 7/2004 | Haight |
| 6,758,975 B2 | 7/2004 | Peabody et al. |
| 6,776,912 B2 | 8/2004 | Baurmeister |
| 6,783,713 B2 | 8/2004 | Tremblay et al. |
| 6,800,200 B2 | 10/2004 | Bassett et al. |
| 6,803,363 B2 | 10/2004 | Polaschegg |
| 6,814,085 B2 | 11/2004 | Brattesani et al. |
| 6,814,724 B2 | 11/2004 | Taylor |
| 6,835,713 B2 | 12/2004 | Montelaro et al. |
| 6,838,005 B2 | 1/2005 | Tepper et al. |
| 6,843,784 B2 | 1/2005 | Modak et al. |
| 6,844,028 B2 | 1/2005 | Mao et al. |
| 6,849,463 B2 | 2/2005 | Santini, Jr. et al. |
| 6,858,139 B2 | 2/2005 | Taylor |
| 6,887,270 B2 | 5/2005 | Miller et al. |
| 6,887,847 B2 | 5/2005 | Montelaro et al. |
| 6,921,390 B2 | 7/2005 | Bucay-Couto et al. |
| 2001/0010016 A1 | 7/2001 | Modak |
| 2001/0049975 A1 | 12/2001 | Howard et al. |
| 2002/0009436 A1 | 1/2002 | Doyle et al. |
| 2002/0015716 A1 * | 2/2002 | Jampani et al. ............ 424/401 |
| 2002/0037260 A1 | 3/2002 | Budny et al. |
| 2002/0051812 A1 | 5/2002 | DiCosmo et al. |
| 2002/0064858 A1 | 5/2002 | Yacoby-Zeevi |
| 2002/0066702 A1 | 6/2002 | Liu |
| 2002/0068093 A1 | 6/2002 | Trogolo et al. |
| 2002/0091424 A1 | 7/2002 | Biel |
| 2002/0102405 A1 | 8/2002 | Chapman et al. |
| 2002/0123787 A1 | 9/2002 | Weiss |
| 2003/0018306 A1 | 1/2003 | Bucay-Couto et al. |
| 2003/0065292 A1 | 4/2003 | Darouiche et al. |
| 2003/0068667 A1 | 4/2003 | Olson et al. |
| 2003/0105143 A1 | 6/2003 | Ammenodola et al. |
| 2003/0134783 A1 | 7/2003 | Harshey et al. |
| 2003/0153983 A1 | 8/2003 | Miller et al. |
| 2003/0175812 A1 | 9/2003 | Reppy et al. |
| 2003/0176367 A1 | 9/2003 | Cali et al. |
| 2003/0176848 A1 | 9/2003 | Gibson et al. |
| 2003/0206875 A1 | 11/2003 | Budny et al. |
| 2003/0215433 A1 | 11/2003 | Kokai-Kun et al. |
| 2003/0224032 A1 | 12/2003 | Read et al. |
| 2003/0229065 A1 | 12/2003 | Levy et al. |
| 2004/0044299 A1 | 3/2004 | Utsugi |
| 2004/0106912 A1 | 6/2004 | Rosinskaya et al. |
| 2004/0109852 A1 | 6/2004 | Xu |
| 2004/0115721 A1 | 6/2004 | Mao et al. |
| 2004/0116845 A1 | 6/2004 | Darouiche et al. |
| 2004/0116896 A1 | 6/2004 | Massengale |
| 2004/0122511 A1 | 6/2004 | Mangiardi et al. |
| 2004/0126897 A1 | 7/2004 | Prince et al. |
| 2004/0132164 A1 | 7/2004 | Doyle et al. |
| 2004/0132217 A1 | 7/2004 | Prince et al. |
| 2004/0172000 A1 | 9/2004 | Roe et al. |
| 2004/0180829 A1 | 9/2004 | Bassler et al. |
| 2004/0188351 A1 | 9/2004 | Thiele et al. |
| 2004/0230162 A1 | 11/2004 | Tan |
| 2004/0235914 A1 | 11/2004 | Ammendola et al. |
| 2004/0249441 A1 | 12/2004 | Miller et al. |
| 2004/0254545 A1 | 12/2004 | Rider et al. |
| 2005/0008671 A1 | 1/2005 | Antwerp |
| 2005/0010158 A1 | 1/2005 | Brugger et al. |
| 2005/0020960 A1 | 1/2005 | Brugger et al. |
| 2005/0020961 A1 | 1/2005 | Burbank et al. |
| 2005/0037498 A1 | 2/2005 | Ribi |
| 2005/0038376 A1 | 2/2005 | Zumeris et al. |
| 2005/0038498 A1 | 2/2005 | Dubrow et al. |
| 2005/0048124 A1 | 3/2005 | Sarangapani |
| 2005/0049181 A1 | 3/2005 | Madhyastha |
| 2005/0059731 A1 | 3/2005 | Albrecht et al. |
| 2005/0085775 A1 | 4/2005 | Ostfeld et al. |
| 2005/0085777 A1 | 4/2005 | Tan |
| 2005/0090785 A1 | 4/2005 | Tan |
| 2005/0095351 A1 | 5/2005 | Zumeris et al. |
| 2005/0100937 A1 | 5/2005 | Holmes |
| 2005/0101841 A9 | 5/2005 | Kaylor et al. |
| 2005/0118239 A1 | 6/2005 | Sabesan |
| 2005/0124678 A1 | 6/2005 | Levy et al. |
| 2005/0131332 A1 | 6/2005 | Kelly et al. |
| 2005/0131356 A1 | 6/2005 | Ash et al. |
| 2005/0137536 A1 | 6/2005 | Gonnelli |
| 2005/0142622 A1 | 6/2005 | Sanders et al. |
| 2005/0143286 A1 | 6/2005 | Singh et al. |
| 2005/0154448 A1 | 7/2005 | Cully et al. |
| 2005/0158253 A1 | 7/2005 | Budny et al. |
| 2005/0161859 A1 | 7/2005 | Miller et al. |
| 2005/0171501 A1 | 8/2005 | Kelly |
| 2005/0192590 A1 | 9/2005 | Feeley et al. |
| 2005/0199245 A1 | 9/2005 | Brennan |
| 2005/0209547 A1 | 9/2005 | Burbank et al. |
| 2005/0220837 A1 | 10/2005 | Disegi et al. |
| 2005/0221072 A1 | 10/2005 | Dubrow et al. |
| 2005/0233950 A1 | 10/2005 | Madhyastha |
| 2005/0256502 A1 | 11/2005 | DiMatteo et al. |

* cited by examiner

US 7,488,757 B2

INVISIBLE ANTIMICROBIAL GLOVE AND HAND ANTISEPTIC

This application is 371 of PCT/US04/009009, filed 24 Mar. 2004, which claims priority from provisional application No. 60/457,054, filed 24 Mar. 2003.

BACKGROUND OF THE INVENTION

1. Field of the Invention

The present invention relates to an alcohol-based antiseptic surgical scrub, which leaves an anti-microbial invisible film or "glove" on the hands, following alcohol evaporation.

2. Description of Related Art

Diligent hand washing and the wearing of gloves by healthcare professionals are essential components of effective infection control in the healthcare environment. Healthcare professionals regularly wash their hands and wear gloves to control the spread of bacteria and infection from patient to patient, and to themselves.

Hand washing procedures are performed in several ways and include products such as an ordinary anti-microbial bar soap, skin disinfecting or pre-operative agents or rubbing alcohol. Such procedures and products contain anti-microbial agents such as alcohol, iodine, chlorhexidine digluconate, chloroxylenol, triclosan and hexachlorophenes. Gloving by the healthcare workers is a normal practice in the hospital setting to create a barrier that protects themselves and the patient from transmitted bacteria.

Healthcare workers commonly use scrub brushes impregnated with anti-microbial agents for antiseptic hand washing prior to surgical procedures and other invasive patient care procedures. These impregnated scrub brushes have proven to be an effective method of reducing the spread of infection in the healthcare setting. Anti-microbial solutions are specially designed for use in the scrub brush where the mechanical action of scrubbing with the brush creates a foam or lather. Before performing a surgical procedure, the surgical team uses surgical scrubs to disinfect their hands with such a standardized scrub procedure, usually lasting 5 to 10 minutes, then don sterile gloves before initializing the surgical procedure.

Alcohols, in general, are recognized for their disinfection properties. Rubbing alcohol, containing 70% ethyl alcohol (Formula 23-H) and 30% water, and isopropyl rubbing alcohol, containing 70% isopropyl alcohol and 30% water, are commonly used disinfectants. Alcohol is a potent anti-microbial agent, and, if used with surgical scrub, will cause significant mean log reduction of bacterial counts on the hands of healthcare workers. However, the use of alcohols for surgical scrubs has never become popular in the United States of America, even though the compound has very good properties for immediate reduction of microbial flora on the hands. This may be due to the fact that alcohol is a defatting agent. When applied to the human skin, it can make the skin very dry, often leading to chapped and cracked skin. These characteristics thus often result in difficult and painful sensitivity for the users.

The prior art includes many examples of varying antiseptic skin cleaners and wipes, some of which include alcohol. U.S. Pat. No. 4,678,606 discloses a personal liquid cleaning composition having a primary surfactant selected from the group of anionic, cationic, zwitterionic, amphoteric and semipolar surfactants, an auxiliary surfactant selected from certain ethoxylated aliphatic alcohols and a water-soluble polymeric thickening agent. U.S. Pat. No. 4,374,126 discloses an alcohol insoluble antimicrobial topical lotion including a lower acrylate interpolymer. U.S. Pat. No. 5,512,199 discloses an antimicrobial hand wipe which includes an alcohol. U.S. Pat. No. 6,180,584 is directed to a film forming antimicrobial composition. Notably, this composition is an alcohol-free anti-microbial skin sanitizing composition.

However, none of these prior art products provide the benefits of the presently disclosed surgical scrub composition, which not only includes alcohol, but also provides the desired invisible, anti-microbial long-lasting film on the hands following solvent evaporation.

SUMMARY OF THE INVENTION

The present invention is an alcohol based hand surgical scrub, which includes dual anti-microbial agent preservatives, cationic polymer film-forming agents and provides a long term residual, anti-microbial "invisible glove" on the skin. The composition desirably comprises an alcohol, anti-microbial agent which prevents the growth of bacteria and a polymer system to form a barrier on the skin. The polymer system creates an invisible film on the skin following solvent evaporation. This invisible film provides a lasting anti-microbial barrier on the skin.

The composition desirably includes an alcohol, a positive charged anti-microbial agent, skin emollients and lubricants and a film-forming polymer system. The composition may also include one or both of methyl and propyl parabens and silicone. The anti-microbial agents prevent bacteria from growing back to the baseline of the normal skin flora population. The surgical scrub composition contains chemical ingredients to remove extraneous matter and organisms from the hands. Skin emollients and lubricants are also provided to prevent the defatting effect of the alcohol, thereby eliminating the dry, chapped feeling on the skin. Additional or complimentary anti-microbial agents are preferably included to serve as preservative and persistent active agents. These anti-microbial agents in the composition will improve the anti-microbial characteristics of the formulation and provide a long-term residual activity for the skin. As previously noted, the polymer system is included to create an invisible film after the solvent is evaporated. This invisible film acts as a physical anti-microbial barrier or "glove" to protect the healthcare worker's hands. This film has an anti-microbial effect at least for six hours to prevent and kill the bacteria on the healthcare worker's hands.

DESCRIPTION OF THE PREFERRED EMBODIMENT(S)

This invention may be satisfied by embodiments in many different forms, and is not limited to any specific or preferred embodiments of the invention, which are merely exemplary of the principles of the invention. Various other modifications will be apparent to and readily made by those skilled in the art without departing from the scope and spirit of the invention. The scope of the invention will be measured by the appended claims and their equivalents.

The surgical scrub composition of the present invention includes alcohol, a positive-charged anti-microbial agent, skin emollients and lubricants, and a cationic polymer film-forming thickening agent.

One or more alcohols are utilized in the surgical scrub composition due to alcohol's well known germicidal properties. Alcohols which may be used in the present composition include isopropyl alcohol, ethanol, and n-propanol. In the most preferred embodiment, ethyl alcohol is used. Preferably, alcohol is present in the surgical scrub composition in an amount from about 60 to about 95 weight percent, and most preferably, at about 71 weight percent.

Emollients are utilized in the surgical scrub composition of the present invention to lessen the drying effect of the alcohol on the skin. A preferred emollient is isopropyl palmitate, which is an ester emollient available from Amerchol Corporation of Edison, N.J. When used on the skin, isopropyl palmitate leaves a soft, non-sticky feel to the skin. Isopropyl palmitate is a lipophillic emollient, an oily, fatty substance which is water insoluble. Lanolin and its derivatives are a large group of fatty materials with active emollient properties that can be utilized as emulsifiers or lubricants in the composition.

The preferred embodiment includes glycerin as a hydrophilic emollient and a humectant to maintain the water in equilibrium. Glycerin is available from Spectrum Quality products. Glycerin is a water and alcohol soluble emollient that provides skin conditioning properties to the composition. In another embodiment, propylene glycol may be substituted for glycerin. Preferably, glycerin is present in the surgical scrub composition, by weight percent of the entire composition, in an amount of from about 0.1% to about 5%, and most preferably, about 1.4%.

The surgical scrub composition further includes a silicone fluid. Preferably, the silicone fluid is dimethicone copolyol, cyclomethicone and dimethicone. Most preferably, dimethicone is utilized. Dimethicone 350 is commercially available from General Electric Corporation. Silicone fluids provide good lubricating, aesthetic and occlusive action on the skin. Silicone fluids not only lubricate the skin surface, they also act as a gas barrier to reduce water vapor transmission. Silicone fluids are water and gas insoluble. Preferably, the silicone fluid is present in the surgical scrub composition, by weight percent of the entire composition, in an amount from 0 to about 5%, and most preferably, about 0.03%.

Most hydrocarbons are derived from petrolatum crude by a fractional distillation process. Such hydrocarbons function as emollients due to their ability to lubricate and hold water at the skin surface due to their relative occlusivity. Mineral oil and isopropyl palmitate are included in the most preferred embodiment. Despite its lack of aesthetic properties, petrolatum may be utilized. Alternatively or additionally, lanolin derivatives may be included. Preferably, mineral oil is present in the surgical scrub composition, by weight percent of the entire composition, in an amount from 0 to about 5%, and most preferably, about 0.2%. Preferably, isopropyl palmitate is present in the surgical scrub composition, by weight percent of the entire composition, in an amount from about 0.1% to about 5%, and most preferably about 0.4%.

Preferably, the surgical scrub composition includes about 0.1% to about 5% of an emollient or emollients.

An anti-microbial agent is included in the surgical scrub composition to kill microorganisms and prevent or inhibit their growth and reproduction. In the absence of an antimicrobial agent, microbial flora will grow on the skin following alcohol evaporation. The antimicrobial agents present in the surgical scrub composition are selected to be compatible with the chemical and physical properties of the skin. In addition, the antimicrobial agent should be non-toxic and environmentally friendly.

As previously noted, the alcohol component of the surgical scrub composition is an excellent antimicrobial agent. It also acts as a preservative. However, following application of the surgical scrub composition, the alcohol will evaporate from the skin over time. In the most preferred embodiment, the residue remaining on the skin following alcohol evaporation will include an amount of an antimicrobial agent which also acts as a preservative. Suitable antimicrobial agents which act as preservatives may be selected from the class of phenols including para-chloro-meta-xylenol, bis-biguanides such as chlorhexidine digluconate, chlorhexidine diacetate or quaterium class such as benzethonium chloride, benzalkonium chloride. Chloroxylenol, triclosan, hexachlorophenes, octenidine and quarternary compounds may be included. Hexetidine, germaben II, kathon CG, triclosan are other antimicrobial agents may also be suitable as preservatives. Benzethonium chloride and benalkonium chloride (as hyamine 3500) are available from Lonza Inc., chlorhexidine digluconate is available from Xttrium Laboratories, germaben II is available from Sutton Laboratories. In a most preferred embodiment, benzethonium chloride, chlorhexidine digluconate (20%) and benzelkonium chloride (80%) are present. Preferably, benzethonium chloride is present in the scrub composition, by weight percent of the entire composition, in an amount from about 0.05% to about 5%, and most preferably, about 0.09%. Preferably, chlorhexidine digluconate (20%) is present in the surgical scrub composition, by weight percent of the entire composition, in an amount from about 0.05% to about 5%, and most preferably about 0.45%. Preferably, benzalkonium chloride (80%) is present in the surgical scrub composition, by weight percent of the entire composition, in an amount from 0 to about 5%, and most preferably, about 0.09%. Preferably, the composition includes about 0% to about 5% of an anti-microbial agent.

Methylparaben and propylparaben (both available from Mallinckrodt Chemical Company) are desirably included in the surgical scrub composition as preservatives. These are further desired for their moisturizing and film forming characteristics. Preferably, methylparaben is contained in the surgical scrub composition, by weight percent of the entire composition, in an amount from about 0 to about 5%, and most preferably about 0.03%. Preferably, propylparaben is present in the surgical scrub, by weight percent of the entire composition, in an amount from about 0 to about 5%, and most preferably, about 0.03%. One or both of these compositions are preferably included in the amount of about 0% to about 5% of the surgical scrub composition.

To create the desired residual film of the surgical scrub composition, cationic polymer thickening agents are employed. Thickening agents must be soluble in the alcohol and compatible with cationic ingredients. The cationic polymer thickening agents are preferably present in the surgical scrub composition, by weight percent of the entire composition, in the amount of about 0.1% to about 5%.

Incroquat behenyl TMS is most preferably used as a cationic polymer. It is a strong conditioning agent and an outstanding cationic emulsifier. This composition bonds to the skin due to the skin's negative charge. Incroquat behenyl TMS is a compound of 25% active solution of behenyl trimonium methosulfate in cetearyl alcohol and is available in flaked/pastel form and supplied by Croda Inc. Incroquat CR concentrate is preferably used as an additional cationic polymer. Incroquat CR concentrate is available from Croda Inc. and is comprised of cetearyl alcohol, castor oil and stearalkonium chloride. This composition is a one-part formulating aid. It is a conditioner and self-emulsifier. The desired combination of the incroquat behenyl TMS and incroquat CR concentrate provides a smooth feel to the skin and neutralizes the static charge of the human skin. Preferably, incroquat BTMS is present in the surgical scrub composition, by weight percent of the entire composition, in an amount from about 0.1% to about 5%, and most preferably about 0.4%. Preferably, incroquat CR is present in the surgical scrub composition, by weight percent of the entire composition, in an amount from 0 to about 5%, and most preferably about 0.1%.

Alternative or additional polymers include cellulose, polyvinylpyrolidone and waxes.

The most preferred embodiment of the surgical scrub composition is as follows:

|  | % of Total (w/w) |
| --- | --- |
| 1-Docosanol | 1.00% |
| Benzethonium Chloride | 0.09% |
| Chlorhexidine Digluconate, (20%) | 0.45% |
| Dimethicone | 0.03% |

-continued

| | % of Total (w/w) |
|---|---|
| Ethyl Alcohol | 71.00% |
| Glycerin | 1.40% |
| Benzalkonium Chloride | 0.09% |
| Incroquat BTMS | 0.40% |
| Incroquat CR | 0.10% |
| Isopropyl Palmitate | 0.40% |
| Mineral Oil | 0.20% |
| Methylparaben | 0.03% |
| PEG-10 Behenyl Ether | 1.50% |
| Propylparaben | 0.03% |
| Purified Water | 23.28% |

The most preferred embodiment includes the additional components 1-Docosanol as a moisturizer and film forming substance, PEG-10 behenyl ether as a moisturizer, fragrance and water. Preferably, 1-Docosanol is present in the surgical scrub composition, by weight percent of the entire composition, in an amount from about 0.1% to about 5%, and most preferably about 1%. Preferably, PEG-10 behenyl ether is present in the surgical scrub composition, by weight percent of the entire composition, in an amount from about 0.1% to about 5%, and most preferably about 1.5%. Preferably, purified water is present in the surgical scrub composition, in an amount from about 1% to about 35%, and most preferably about 23%.

The surgical scrub composition does not cause skin irritation or sensitization. Additional advantages of the composition include its compatibility with positive-charged anti-microbial agents such as chlorhexidine digluconate, thus ensuring the effectiveness of the anti-microbial agent or agents. The included skin emollients and lubricants eliminate skin drying or chapping. These compositions counteract the defatting effect of the alcohol.

The surgical scrub composition includes anti-microbial agents, which act as both persistent active agents and suitable preservatives. This composition permits a very small amount of an anti-microbial agent to improve anti-microbial activities and provide long-term residual activity for the skin.

Traditionally, healthcare workers have scrubbed prior to every surgical procedure. An improved method may be to apply water to the skin, perform hand scrubbing at the beginning of the day using a scrub brush and anti-microbial scrub solution, rinsing the anti-microbial scrub solution with water, and then utilization of the composition of the present invention prior to subsequent surgical procedures. A high level of hand antisepsis can be achieved via this method without abrasive scrubbing multiple times a day.

EXAMPLES

The following examples are not intended to limit the scope of the invention, but are only intended to be exemplary in nature.

Standard testing of the most preferred embodiment demonstrates its effectiveness as an antiseptic to provide an immediate reduction of microbes and then to prevent microbial growth back to baseline within a 6-hour period. The immediate log reduction was 2.65 on day 1, 2.92 on day 2 and 3.04 on day 3. The residual effect was a log reduction six hours after hand cleaning of 1.45 on day 1, 1.79 on day 2 and 2.18 on day 3. The residual anti-microbial activity is facilitated by the containment of the anti-microbial agent in the polymer film that is formed. The film forms an invisible "glove" containing an anti-microbial agent. The anti-microbial agent remains on the skin in the film and continues to be bactericidal over extended periods of time. The invisible glove prevents microbes that may be present on the hands of the healthcare worker from infecting a patient and the glove also provides a barrier for microbes infecting the healthcare worker from the patient.

Through testing, the composition has been shown to exceed industry standards. The critical indices for this study were an immediate one (1) $\log_{10}$ reduction in microorganisms on Day 1; an immediate two (2) $\log_{10}$ reduction in microorganisms on Day 2; an immediate three (3) $\log_{10}$ reduction in microorganisms on Day 5; and that microorganism populations from the approximately three (3) hour to three (3) hour and thirty (30) minute AND approximately six (6) hour to six (6) hour and thirty (30) minute samples not return to baseline level. Refer to Table I.

TABLE I

Statistical Summary of the $\log_{10}$ Recovery Values of Most Preferred Embodiment

| Sample | Sample Size | Mean | Standard Deviation | 95% Confidence Interval | $\log_{10}$ Reduction from Baseline | TFM (1994) Required $\log_{10}$ Reduction |
|---|---|---|---|---|---|---|
| Baseline | 36 | 6.01 | 0.40 | 5.88 to 6.15 | N/A | |
| Day 1, Immediate | 12 | 3.36 | 0.68 | 2.93 to 3.79 | 2.65 | 1 |
| Day 1, 3 Hour | 12 | 4.08 | 0.99 | 3.45 to 4.71 | 1.93 | No return to baseline |
| Day 1, 6 Hour | 12 | 4.56 | 0.68 | 4.13 to 4.99 | 1.45 | No return to baseline |
| Day 2, Immediate | 11 | 3.09 | 0.53 | 2.74 to 3.45 | 2.92 | 2 |
| Day 2, 3 Hour | 11 | 3.73 | 0.90 | 3.12 to 4.34 | 2.28 | No return to baseline |
| Day 2, 6 Hour | 12 | 4.22 | 0.81 | 3.70 to 4.73 | 1.79 | No return to baseline |
| Day 5, Immediate | 10 | 2.97 | 0.47 | 2.63 to 3.31 | 3.04 | 3 |
| Day 5, 3 Hour | 11 | 3.50 | 0.61 | 3.09 to 3.91 | 2.51 | No return to baseline |
| Day 5, 6 Hour | 11 | 3.83 | 1.01 | 3.15 to 4.51 | 2.18 | No return to baseline |

The most preferred embodiment was also tested in conjunction with a standard hand scrub utilizing a brush impregnated with an anti-microbial agent. The composition was applied to the hands of the test subjects one-half hour following the standard scrub. Test results showed an increased log reduction of microbes when the scrubbing and the preferred composition were used together. Log reductions of microbes were 3.66 for Day 1, 3.98 for Day 2, and 3.81 for Day 3. Residual activity was also increased with log reductions after six hours of 2.31 for Day 1, 3.52 for Day 2 and 3.70 for Day 3. Use of the preferred composition in conjunction with a standard scrub exceeded industry standards for anti-microbial compositions. Refer to Table II and FIG. 1.

TABLE II

Figure 1:
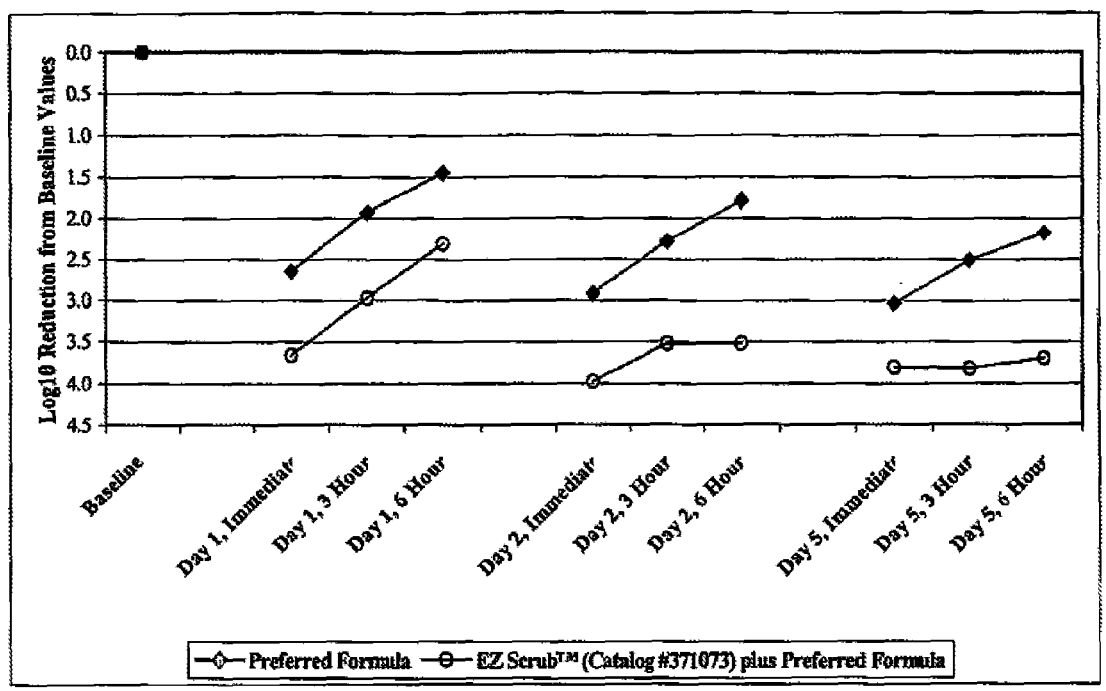
FIG. 1 is a graphical presentation of the $\log_{10}$ reductions from baseline for the preferred formula and BD E-Z Scrub™ [BD Catalog #371073] plus the most preferred embodiment.

Statistical Summary of the $\text{Log}_{10}$ Recovery Values Using BD E-Z Scrub ™ Catalog #371073 Plus Most Preferred Embodiment

| Sample | Sample Size | Mean | Standard Deviation | 95% Confidence Interval | $\text{Log}_{10}$ Reduction from Baseline | TFM (1994) Required $\text{Log}_{10}$ Reduction |
|---|---|---|---|---|---|---|
| Baseline | 38 | 6.10 | 0.38 | 5.97 to 6.22 | N/A | |
| Day 1, Immediate | 12 | 2.88 | 0.46 | 2.15 to 2.73 | 3.66 | 1 |
| Day 1, 3 Hour | 13 | 3.13 | 0.79 | 2.65 to 3.60 | 2.97 | No return to baseline |
| Day 1, 6 Hour | 13 | 3.79 | 0.88 | 3.26 to 4.32 | 2.31 | |
| Day 2, Immediate | 12 | 2.12 | 0.35 | 1.90 to 2.34 | 3.98 | 2 |
| Day 2, 3 Hour | 12 | 2.58 | 0.93 | 1.99 to 3.17 | 3.52 | No return to baseline |
| Day 2, 6 Hour | 12 | 2.58 | 0.66 | 2.16 to 3.00 | 3.52 | |
| Day 5, Immediate | 10 | 2.29 | 0.37 | 2.02 to 2.55 | 3.81 | 3 |
| Day 5, 3 Hour | 10 | 2.28 | 0.32 | 2.05 to 2.51 | 3.82 | No return to baseline |
| Day 5, 6 Hour | 12 | 2.40 | 0.49 | 2.09 to 2.71 | 3.70 | |

The invention claimed is:

1. A surgical scrub composition comprising, in weight percent of the total composition:
   (a) from about 0.1% to about 5% of 1-docosanol;
   (b) from about 0.05% to about 5% of chlorhexidine digluconate;
   (c) from about 60% to about 95% of alcohol;
   (d) from about 0.1% to about 5% of glycerin;
   (e) from about 0.1% to about 5% of a 25% active solution of behenyl trimethyl ammonium methosulfate in cet-earyl alcohol;
   (f) from about 0.1% to about 5% of isopropyl palmitate;
   (g) from about 0.03% to about 5% of a preservative selected from the group consisting of methylparaben and propylparaben; and
   (h) from about 1% to about 35% of purified water.

2. A method of using a surgical scrub composition for hand antisepsis comprising:
   (a) applying a cleansing liquid to the skin;
   (b) scrubbing the skin with an anti-microbial scrub solution;
   (c) rinsing the anti-microbial scrub solution from the skin; and
   (d) applying an effective amount of a surgical scrub composition according to claim 1.

* * * * *